(12) United States Patent
Ducrocq et al.

(10) Patent No.: US 6,436,984 B1
(45) Date of Patent: Aug. 20, 2002

(54) MELATONIN DERIVATIVES AND MEDICINE CONTAINING SAME

(75) Inventors: Claire Ducrocq, Orsay; Béatrice Blanchard, Reuil-Malmaison, both of (FR)

(73) Assignee: Centre National de la Recherche Scientifique (CNRS), Paris Cedex (FR)

( * ) Notice: Subject to any disclaimer, the term of this patent is extended or adjusted under 35 U.S.C. 154(b) by 0 days.

(21) Appl. No.: 09/868,168

(22) PCT Filed: Dec. 16, 1999

(86) PCT No.: PCT/FR99/03163
§ 371 (c)(1),
(2), (4) Date: Aug. 29, 2001

(87) PCT Pub. No.: WO00/37441
PCT Pub. Date: Jun. 29, 2000

(30) Foreign Application Priority Data

Dec. 18, 1998 (FR) .............................. 98 16015

(51) Int. Cl.[7] .................. A61K 31/4045; C07D 209/18
(52) U.S. Cl. ....................... 514/419; 548/483
(58) Field of Search ........................... 548/483; 514/419

(56) References Cited

FOREIGN PATENT DOCUMENTS

| | | |
|---|---|---|
| EP | 0 513 702 A2 | 11/1992 |
| EP | 0 543 659 A1 | 5/1993 |
| FR | 2 753 095 | 3/1998 |
| WO | 97/06140 | 2/1997 |
| WO | 98/09653 | 3/1998 |

*Primary Examiner*—Joseph K. McKane
*Assistant Examiner*—Rebecca Anderson
(74) *Attorney, Agent, or Firm*—Foley & Lardner

(57) ABSTRACT

The invention concerns melatonin derivatives of formula (I) wherein: $R_1$ represents H, a $C_1$–$C_4$ alkyl group or a $C_1$–$C_4$ alkoxy group; $R_2$ represents H or a $C_1$–$C_4$ alkyl group; $R_3$ represents H, methyl or a halogen atom; $R_4$, $R_5$ represent individually H or a halogen atom; $R_6$ represents H or a $C_1$–$C_4$ alkyl group, or a pharmaceutically acceptable salt thereof. The invention also concerns a medicine comprising said derivatives.

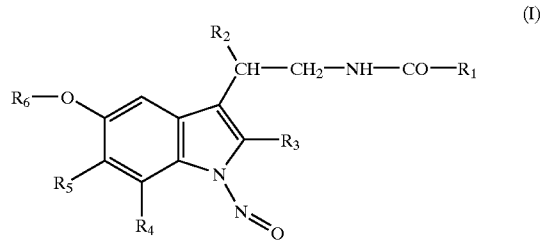

8 Claims, 1 Drawing Sheet

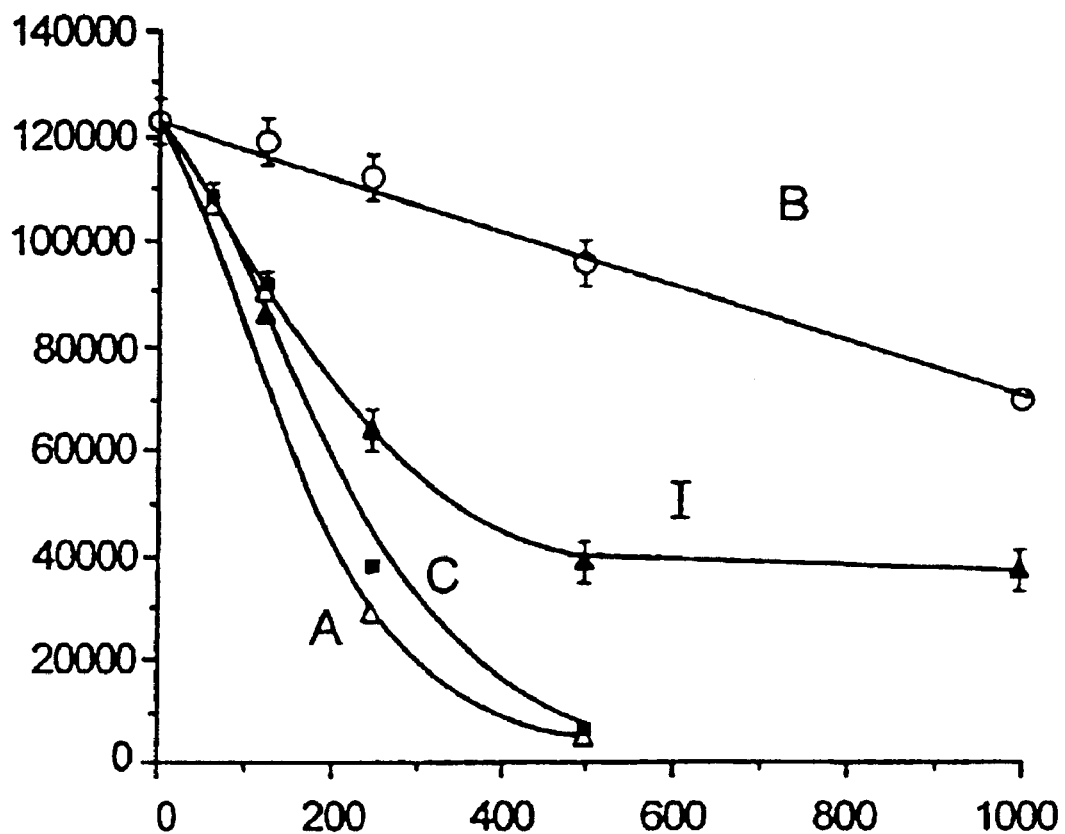

MELATONIN DERIVATIVES AND MEDICINE CONTAINING SAME

As provided for in 35 USC § 120 and 35 USC § 365, the right of priority is claimed based on international application PCT/FR99/03163, filed Dec. 16, 1999, and French Application 98/16,015, filed Dec. 18, 1998, to which the international application claims the benefit of priority.

The present invention relates to novel melatonin derivatives capable of releasing nitrogen monoxide (NO) and melatonin under physiological conditions.

Another subject matter of the invention is these melatonin derivatives for their application as therapeutically active substances.

Nitrogen monoxide is a product of NO-synthetases in all animal organs, where it plays varied roles in maintaining the physiological functions, but especially in pathological situations, where it is synthesized in much greater amounts. It is a vasodilator and an antiaggregant for platelets and leukocytes with other cell types. It is involved in nerve transmissions, neither cholinergic nor adrenergic, but also in excitotoxicity processes of glutamate in the nervous system. In neurodegenerative processes, it is still difficult to take into consideration the involvement of NO and/or of oxygen derivatives. According to several authors, NO would rather have a protective role with regard to the neurons and would have an antioxidizing role by combining with oxygenated radicals. However, when it binds to superoxide, it generates peroxynitrite, which, in turn, modifies macromolecules and very particularly DNA. The fragmentation of DNA constitutes a phase in the apoptosis process.

As NO is an excellent scavenger of superoxide anions with the generation of peroxynitrite, protection of tissues can only be ensured in the presence of compounds capable of scavenging peroxynitrite, such as melatonin.

Melatonin or N-acetyl-5-methoxytryptamine is a hormone synthesized in the pineal gland and in the retina, especially during the night and in young animals. Its level decreases with age and during the development of Alzheimer's disease. It controls the physiological functions associated with the circadian rhythm and is involved in the immune response.

It has recently been proposed that its essential role is to scavenge radicals and strong oxidants. These interactions do not require recognition with specific receptors but are involved in the physiopathological processes of the living world. This hypothesis is based on direct experimental results but also on the effects of melatonin in protecting proteins, membrane lipids and DNA from oxidative damage due to radical processes. In particular, melatonin generally prevents lipid peroxidation, both in vitro and in vivo.

The hydroxyl radical is the major toxic entity originating from oxygen in living organisms. Its level increases with age. It is responsible for the initiation of radical chain reactions which characterize oxidative stress. There exists no specific enzyme system capable of inactivating it, as is the case for the superoxide anion. This is the role of antioxidants (vitamins C and E, glutathione, carotene, and the like). Melatonin is among the most effective of them since it reacts with this radical with a rate close to the diffusion limit. On the other hand, it does not react or reacts very slowly with the superoxide anion.

It is also involved in the redox balance, maintaining the homeostasis of glutathione and initiating the synthesis of genes of antioxidant enzymes.

Its properties make it possible to explain why melatonin reduces the toxicity of glutamate in neuronal cultures and the undesirable effects during anticancer chemotherapies. In this case, these therapeutic effects are additional to its oncostatic properties observed with respect to cultures of human cancer cells and with respect to certain cancers.

Finally, recent results seem encouraging for the use of melatonin in the prophylaxis of the appearance of gastric ulcers and of migraine.

Among the NO donors currently known, only diazeniumdiolates, generally known as NONOates, spontaneously and quantitatively release their nitrosyl groups as NO.

The other NO donors release NO after reductive or oxidative stages. The only ones used as vasodilating medicaments in cardiovascular diseases, organic nitrates and sydnonimines, exhibit complex in vitro and poorly known in vivo decomposition mechanisms. Organic nitrates are metabolized in the walls of the blood vessels. Molsidomine or pirsidomine are hydrolyzed enzymatically in the liver and release active compounds which spontaneously generate NO and the superoxide anion, in vitro.

However, none of these compounds simultaneously releases an antioxidant capable in particular of scavenging peroxynitrite and nitrogen monoxide.

Furthermore, melatonin derivatives used as medicaments are known from patent applications EP-A-513 702 and EP-A-543 659.

It is thus desirable to prepare compounds capable of simultaneously releasing both antioxidants: nitrogen monoxide and an antioxidant capable in particular of scavenging peroxynitrite. Furthermore, such compounds must exhibit a sufficient lipophilic nature to be physiologically acceptable, in particular for crossing the hematoencephalic barrier.

The compounds which are a subject matter of the present invention simultaneously solve the abovementioned problems.

According to the invention, the melatonin derivative corresponds to the formula:

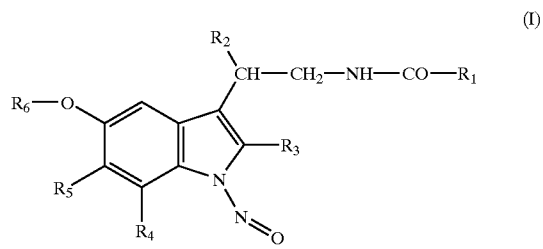

(I)

in which:

$R_1$ represents H, a $C_1$ to $C_4$ alkyl group or a $C_1$ to $C_4$ alkoxy group, $R_2$ represents H or a $C_1$ to $C_4$ alkyl group, $R_3$ represents H, methyl or a halogen atom, $R_4$ and $R_5$ individually represent H or a halogen atom, $R_6$ represents H or a $C_1$–$C_4$ alkyl group, or a pharmaceutically acceptable salt of the latter.

Preferably, $R_2$=H, $R_6$=$CH_3$ and $R_1$=$CH_3$.

According to a preferred alternative form of the invention, the melatonin derivative corresponds to the formula:

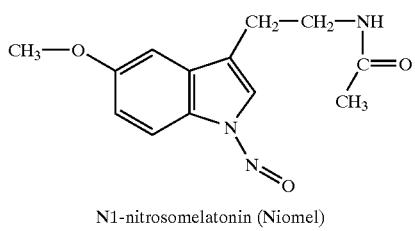

N1-nitrosomelatonin (Niomel)

Another subject matter of the invention is the compounds of formula I or II for their application as therapeutically active substances.

Another subject matter of the invention is a pharmaceutical composition comprising a compound of formula I or II and a pharmacologically acceptable excipient.

Mention is made, among the therapeutic applications, of cardiovascular diseases, ischemia reperfusion injuries, parasitic diseases, inflammatory diseases, neurodegenerative diseases, in particular Alzheimer's disease, myopathies or falciform anemias.

Another subject matter of the invention is a process for the preparation of the melatonin derivatives of formula I, characterized in that a precursor of formula:

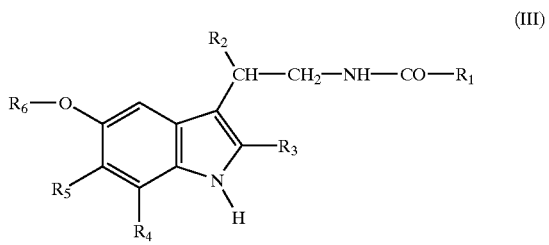

in which $R_1$ to $R_6$ have the same meanings as those indicated for the formula I, is brought into contact, in protic organic solution, with an aqueous sodium nitrite solution and then the mixture is basified, so as to obtain a derivative according to the invention.

The melatonin derivative of formula II is prepared in the following way:

An aqueous sodium nitrite solution is added to a solution, cooled to 4° C., of melatonin in acetic acid and methanol. After basifying with a saturated sodium bicarbonate solution, the N1-nitrosomelatonin is extracted with dichloromethane and the organic solution is dried with magnesium sulfate and then evaporated under reduced pressure. The residue is taken up in ethyl acetate and hexane until crystals are obtained. The crystals are recovered by filtration, dried and stored at ambient temperature with the exclusion of light.

This compound exhibits a melting point of: 138° C.

Chromatographic analysis on a Hypersil C18 column, elution using a gradient of 10 to 50% of acetonitrile and 0.05% of trifluoroacetic acid over 50 minutes, 215 nm detection, results in a peak at 431, whereas the melatonin peak is at 258.

The characteristic band of the light absorption spectrum of the product in phosphate solution from pH 4 to pH 9 is situated at 346 nm.

A significant peak (m/z M+H$^+$=262) is observed by "fast atomic bombardment" mass spectrometry.

The elemental analysis for carbon, proton and nitrogen corresponds to the molar mass 261 and to the formula $C_{13}H_{15}N_3O_3$.

Biological Activity

The biological activity of the derivative of formula I was compared with dipropylenetriamine NONOate (A), melatonin (B) and a dipropylenetriamine NONOate and melatonin (1/2) mixture (C) on the cell preparation of the cell proliferation of the P 815 line.

The cells are incubated with the products in RPMI medium with phenol red for 7 hours. Tritiated thymidine is added after incubating for 3 hours.

BRIEF DESCRIPTION OF DRAWINGS

The results are shown on the curve in the single appended FIGURE, where the concentration of product ($\mu$M) is carried on the abscissa and the radioactivity associated with the DNA (cpm) is carried on the ordinate.

The $IC_{50}$ for the compound of formula I occurs at a concentration of 280 $\mu$M; the $IC_{50}$ for dipropylenetriamine NONOate (A) is 150 $\mu$M.

It is thus found that the melatonin derivative according to the invention displays an activity comparable with that of dipropylenetriamine NONOate.

What is claimed is:

1. A melatonin derivative having formula (I):

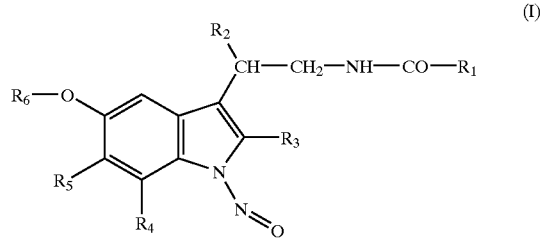

in which:

$R_1$ represents H, a $C_1$–$C_4$ alkyl group or a $C_1$–$C_4$ alkoxy group, $R_2$ represents H or a $C_1$–$C_4$ alkyl group, $R_3$ represents H, methyl or a halogen atom, $R_4$ and $R_5$ individually represent H or a halogen atom, $R_6$ represents H or a $C_1$–$C_4$ alkyl group, or a pharmaceutically acceptable salt of said melatonin derivative.

2. A melatonin derivative according to claim 1, characterized in that $R_2$=H, $R_6$=$CH_3$ and $R_1$=$CH_3$.

3. A melatonin derivative according to claim 2 having formula:

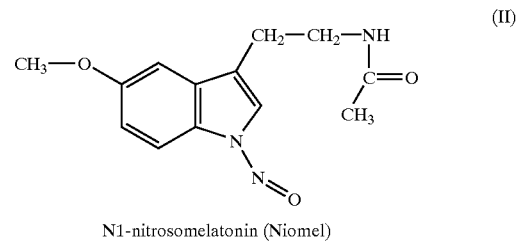

N1-nitrosomelatonin (Niomel)

or a pharmaceutically acceptable salt thereof.

4. A composition, comprising a melatonin derivative of formula I and an active pharmaceutical excipient.

5. A process for the preparation of a melatonin derivative according to claim 1, comprising the steps of:

(i) bringing into contact a precursor having formula:

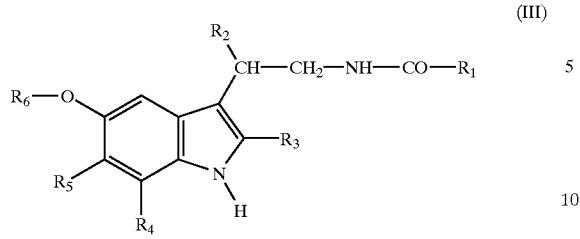

(III)

wherein:

R₁ to R₆ have the same meanings as in claim 1,
with an aqueous sodium nitrite solution, in protic organic solution, and (ii) then basifying the mixture, so as to obtain a derivative according to claim 1.

6. A process of claim 5, wherein said basifying in step (ii) comprises adding a saturated sodium bicarbonate solution.

7. A composition comprising a melatonin derivative according to claim 3 and a pharmaceutical excipient.

8. A method of treating cardiovascular diseases, ischemia reperfusion injuries, parasitic diseases, inflammatory diseases, neurodegenerative diseases, myopathies or falciform anemias comprising:

administering, to a patient in need thereof, a therapeutically effective amount of a compound of formula (I):

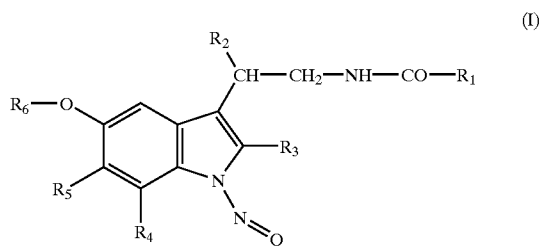

(I)

in which:

$R_1$ represents H, a $C_1$ to $C_4$ alkyl group or a $C_1$ to $C_4$ alkoxy group, $R_2$ represents H or a $C_1$ to $C_4$ alkyl group, $R_3$ represents H, methyl or a halogen atom, $R_4$ and $R_5$ individually represent H or a halogen atom, $R_6$ represents H or a $C_1$–$C_4$ alkyl group, or a pharmaceutically acceptable salt thereof.

* * * * *